US006937955B2

(12) United States Patent
Barnes

(10) Patent No.: US 6,937,955 B2
(45) Date of Patent: Aug. 30, 2005

(54) METHOD FOR AUTOMATIC ALIGNMENT OF METERING SYSTEM FOR A CLINICAL ANALYZER

(75) Inventor: Lawrence Alan Barnes, Honeoye Falls, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 28 days.

(21) Appl. No.: 10/112,543

(22) Filed: Mar. 29, 2002

(65) Prior Publication Data
US 2003/0187600 A1 Oct. 2, 2003

(51) Int. Cl.[7] ............................................. G01C 17/38
(52) U.S. Cl. ............................. 702/94; 702/33; 702/19; 422/63; 422/62; 422/56; 436/43; 436/54; 73/864.01
(58) Field of Search ........................ 702/19, 22, 23, 702/32, 33, 47, 50, 85, 84, 105, 113, 114, 150, 152, 155, FOR 115–119, 123, 124, 134, 143, 145, 147, 144, 156–163, 170, 166; 422/50, 62, 63, 67, 68.1, 100, 919, 920; 436/43, 54, 180; 73/864.01, 863.32, 864.11, 864.21, 864.24, 864.25, 864.31, 864.81

(56) References Cited

U.S. PATENT DOCUMENTS

| | | | |
|---|---|---|---|
| 3,894,438 A | | 7/1975 | Ginsberg |
| 4,190,889 A | | 2/1980 | Etoh et al. |
| 4,281,385 A | | 7/1981 | Nakaso et al. |
| 4,340,390 A | | 7/1982 | Collins et al. |
| 4,631,483 A | * | 12/1986 | Proni et al. .................. 324/71.4 |
| 4,790,183 A | | 12/1988 | Pfost et al. |
| 4,794,085 A | | 12/1988 | Jessop et al. |
| 5,138,868 A | | 8/1992 | Long |
| 5,143,849 A | | 9/1992 | Barry et al. |
| 5,246,316 A | | 9/1993 | Smith |
| 5,270,210 A | * | 12/1993 | Weyrauch et al. ............. 436/43 |
| 5,334,349 A | | 8/1994 | Kelln et al. |
| 5,443,791 A | | 8/1995 | Guiremand et al. |
| 5,465,629 A | | 11/1995 | Waylett, Jr. |
| 5,526,072 A | | 6/1996 | El Hage |
| 5,627,522 A | * | 5/1997 | Walker et al. ............... 340/618 |
| 5,646,049 A | | 7/1997 | Tayi |
| 5,736,403 A | | 4/1998 | Hyde et al. |
| 5,753,512 A | | 5/1998 | Riall et al. |
| 5,846,492 A | * | 12/1998 | Jacobs et al. ................ 422/67 |
| 5,885,530 A | * | 3/1999 | Babson et al. ................ 422/65 |
| 5,939,326 A | * | 8/1999 | Chupp et al. ................. 436/43 |
| 2002/0009391 A1 | * | 1/2002 | Marquiss et al. ............. 422/63 |
| 2002/0176801 A1 | * | 11/2002 | Giebeler et al. .......... 422/82.05 |

OTHER PUBLICATIONS

European Search Report, dated Apr. 5, 2004, for European Appln. No. EP 03 26 1997.

* cited by examiner

Primary Examiner—Marc S. Hoff
Assistant Examiner—Elias Desta
(74) Attorney, Agent, or Firm—Todd J. Burns; Louis J. Capezutto

(57) ABSTRACT

A method for calibrating a clinical analyzer having a dispenser, and for automatically aligning the dispenser of the clinical analyzer includes loading a calibration element at a portion of the clinical analyzer; moving a dispenser of the clinical analyzer in a pre-determined direction (Y) to a position over the calibration element; measuring the height (Z) from the dispenser to the calibration element and determining a position coordinate ($Y_i, Z_i$); storing the position coordinate ($Y_i, Z_i$); determining a maximum height ($Z_{max}$) for the dispenser positioned over the calibration element defined as position coordinate ($Y_{opt}, Z_{max}$); and storing the position coordinate including the maximum height ($Z_{max}$) for the dispenser positioned over the calibration element.

56 Claims, 14 Drawing Sheets

METHOD FOR AUTOMATIC ALIGNMENT OF METERING SYSTEM FOR A CLINICAL ANALYZER

FIELD OF THE INVENTION

The invention relates to the field of clinical analyzers, and more particularly to a novel method for calibrating and automatic alignment of a metering system for a clinical analyzer.

BACKGROUND OF THE INVENTION

In a so-called combinational clinical analyzers a dry chemistry system and a wet chemistry system, for example, can be provided within a contained housing.

Each of the above chemistry systems are somewhat unique in terms of their operation. For example, known "dry" chemistry systems typically include a sample supply which includes a number of sample containers, a metering/transport mechanism, and an incubator having a plurality of test read stations. A quantity of sample is aspirated into a metering tip using a proboscis or probe carried by a movable metering truck along a transport rail. A quantity of sample from the tip is then metered (dispensed) onto a dry slide element which is loaded into the incubator. The slide element is incubated and optical or other reads are taken for analyte detection.

A "wet" chemistry system on the other hand, utilizes a reaction vessel such as a cuvette, into which quantities of patient sample, at least one reagent fluid, and/or other fluids are combined for conducting an assay. The assay is also incubated and tests are conducted for analyte detection. The "wet" chemistry system also includes a metering mechanism to transport patient sample fluid from the sample supply to the reaction vessel.

A number of known clinical analyzers incorporate both wet and dry chemistry systems in a single apparatus. To date, however, there has been no attempt to improve the efficiency/throughput of such devices by effectively linking the chemistry systems of a combinational clinical analyzer together.

Additionally, during the manufacture or field service of a clinical analyzer, it is common to align modules of the system (such as a sample handler, incubator, cuvette holder, etc.) so that the sample metering point on the module is aligned with the sample metering tip of the metering system. This alignment is required to ensure that the sample metering system aspirates the sample correctly, and that it dispenses sample precisely where it is intended. This alignment may be necessary for as many as ten to twenty points within the analyzer, however, the alignment procedure is typically a manual and visual procedure that requires human interaction by a technician. Therefore, the known alignment procedures are quite laborious and have a great degree of subjectivity. Also, these alignment procedures take a significant amount of time to perform and verify.

Accordingly, to date, there have been no known methods that are effective for providing for the automatic alignment of a metering system for a clinical analyzer.

SUMMARY OF THE INVENTION

The present invention is directed toward a method for automatically aligning a dispenser of a clinical analyzer.

The present invention is an automated process for a clinical analyzer that eliminates the need to make subjective adjustments to portions of the clinical analyzer such as a sample tray or a metering system including a dispenser.

In one embodiment, the present invention is directed toward a method for aligning a clinical analyzer having a dispenser, wherein the method comprises the steps of:
  (a) loading a calibration element at a portion of the clinical analyzer;
  (b) moving a dispenser of the clinical analyzer in a predetermined direction (Y) to a position over the calibration element;
  (c) measuring the height (Z) from the dispenser to the calibration element and determining a position coordinate $(Y_i, Z_i)$;
  (d) storing the position coordinate $(Y_i, Z_i)$
  (e) determining a maximum height $(Z_{max})$ for the dispenser positioned over the calibration element defined as position coordination $(Y_{opt}, Z_{max})$; and
  (f) storing the position coordinate including the maximum height $(Z_{max})$ for the dispenser positioned over the calibration element.

Additionally, the method further includes repeating steps (b)–(e) for identifying and storing the position coordinate $(Y_{opt}, Z_{max})$ as well repeating steps (b)–(e) for a plurality of predetermined steps in the Y direction.

The method according to the present invention further includes moving the portion of the clinical analyzer in the X-direction and measuring the height (Z) from the dispenser to the calibration element and determining a position coordinate $(X_i, Y_{opt}, Z_i)$. The method includes moving or stepping the portion of the analyzer in the X-direction until achieving a maximum height $(Z_{max})$.

Upon determining the maximum height $(Z_{max})$ for the dispenser positioned over the calibration element, the position coordinate is defined as $(X_{opt}, Y_{opt}, Z_{max})$ wherein the position coordinate $(X_{opt}, Y_{opt}, Z_{max})$ is used as an alignment point for the dispenser.

Upon calibrating the clinical analyzer in accordance with the method outlined above, in operation, the dispenser is activated for aspirating and dispensing fluid such as sample, reagents, etc. at the established alignment point $(X_{opt}, Y_{opt}, Z_{max})$.

Moreover, the above-identified method in accordance with the present invention is repeated for all desired portions of the clinical analyzer which are required for automatic alignment of the dispenser.

In another embodiment according to the present invention, the present invention is directed to a method for automatically aligning a dispenser of a clinical analyzer, wherein the method comprises the steps of:
  (a) loading a calibration element at a portion of the clinical analyzer;
  (b) moving a dispenser of the clinical analyzer in a predetermined direction (Y) to a position over the calibration element;
  (c) measuring the height (Z) from the dispenser to the calibration element and determining a position coordinate $(Y_i, Z_i)$;
  (d) storing the position coordinate $(Y_i, Z_i)$;
  (e) determining a maximum height $(Z_{max})$ for the dispenser positioned over the calibration element defined as position coordinate $(Y_{opt}, Z_{max})$; and
  (f) storing the position coordinate including the maximum height $(Z_{max})$ for the dispenser positioned over the calibration element.

DETAILED DESCRIPTION

The following description relates to a sample aliquot handler apparatus which is used in conjunction with a specific combinational (ie., wet/dry) clinical analyzer that is used for the testing of biological samples, such as whole blood serum or plasma and more preferably human patient samples.

By "combinational" it is meant that the analyzer includes at least two chemistry systems which can encompass any combination of "dry" and/or "wet" chemistry systems. In brief and in a typical "dry" chemistry system, a patient sample and/or other fluids are aspirated from a fluid supply and deposited onto a dry slide element such as those described in U.S. Pat. No. 3,992,158 to Przyblyowicz et al. The dry slide element is incubated and the amount or presence of at least one analyte in the sample metered onto the element is determined, such as through use of an electrometer, reflectometer or other suitable testing device.

A "wet" chemistry system for purposes of the description which follows includes a reaction vessel which receives predetermined volumetric quantities of sample, reagent, and other fluids which are appropriately metered into the reaction vessel in order to perform an assay(s). The assay is incubated as the fluids are added to the assay(s) and specific analysis is performed, such as through luminescence, light transmissivity, photon detection, and the like using suitable testing apparatus.

Several other terms are used throughout the discussion including the terms "metering tips" and "micro-tips". For purposes of this description, a metering tip refers to a fluid aspirating/dispensing member which can be attached to a proboscis as used in a metering mechanism. The tip includes an open top end and a bottom dispense end and is capable of retaining a volumetric quantity of fluid. Metering tips in and of themselves are repletely well known in the field. A "micro-tip" for purposes of this discussion refers to a metering tip which fits the definitional requirements set forth above. In addition, this tip is sized to retain a smaller (micro) volume of fluid. Moreover, the micro-tip can be fitted within the confines of the metering tip for advantages which will be apparent below.

The analyzer which is described herein is a combinational analyzer having a single "dry" chemistry system and a single "wet" chemistry system. It will be readily understood from the discussion which follows, however, that several variations and modifications are possible which embody the essential concepts of the present invention. For example, the analyzer can include a pair of dry chemistry systems.

Figure 1:
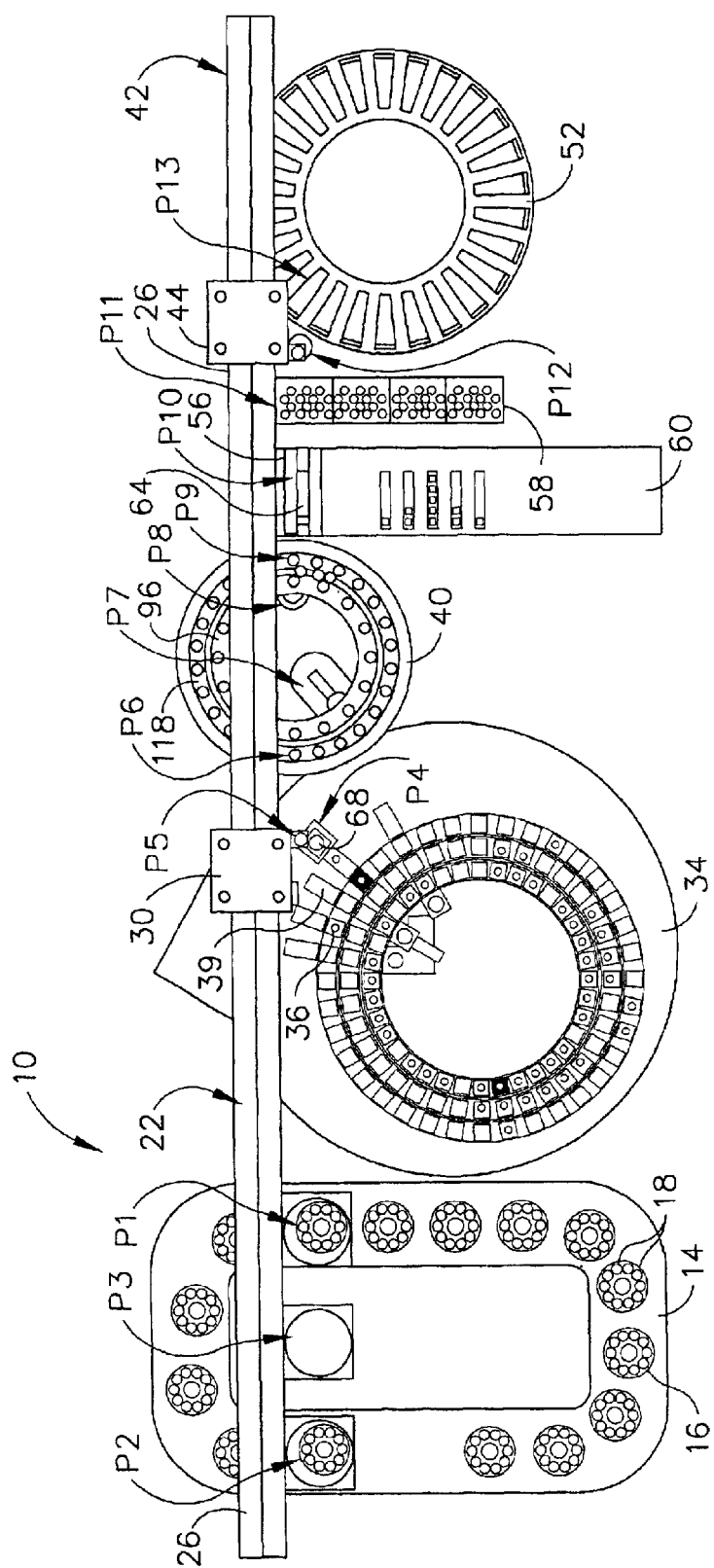
FIG. 1 is an operational block diagram of a combinational wet/dry clinical analyzer including a plurality of stations that interact with a metering system according to the present invention.
Figure 2:
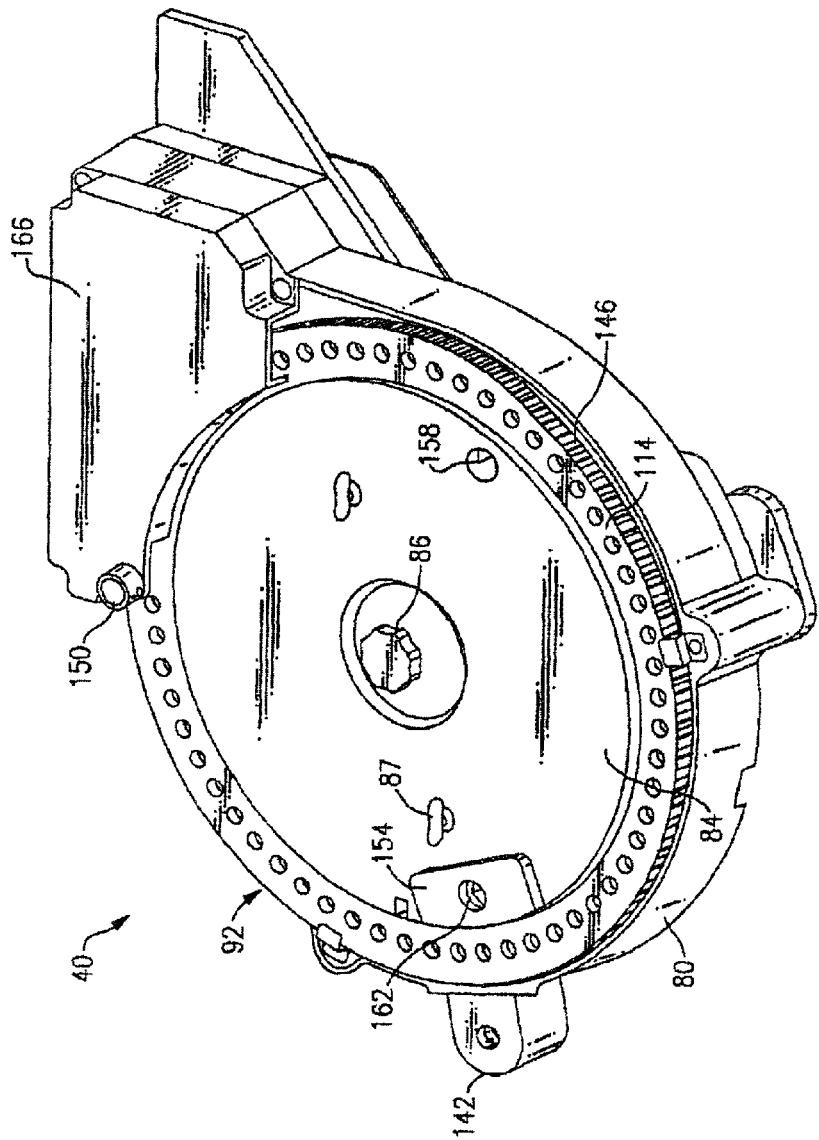
FIG. 2 is a top perspective view of the sample aliquot handler of FIG. 1.

Referring to FIG. 1, there is shown an automated combinational clinical analyzer 10 having a number of component systems which are briefly discussed to provide adequate background for the invention. The analyzer 10 includes a primary sample handler 14 that retains a plurality of primary sample containers 18, a primary metering mechanism 22 which includes a metering transport rail 26 and a metering truck 30 which is movable along the transport rail between a number of stations. Among the stations disposed along the travel path of the metering mechanism 22 are a metering station 68 for a first incubator assembly 34. At the metering station 68, a quantity of sample can be deposited onto a dry slide element which is then shuttled into the incubator assembly 34. The incubator assembly 34 includes at least one read station including a testing device for correlated analyte detection, such as reflectometer (not shown) or an electrometer (not shown). The preceding components each comprise a dry chemistry system for the herein described automated combinational analyzer 10.

Still referring to FIG. 1, the analyzer 10 further includes a secondary metering mechanism 42 that includes a metering truck 44 which is also movable along the metering transport rail 26, a reagent wheel 52 which includes a plurality of containers of at least one reagent fluid, a second incubator assembly 56, a micro-tip supply 58, and a reaction vessel conveyor 60 which carries a plurality of reaction vessels 64. These components have merely been listed in this portion of the discussion. Details relating to their features will be additionally supplied in a later portion of the discussion. For purposes of this description, however, each of the above-noted components define a wet chemistry system for the herein described combinational analyzer 10.

As introduced above, the primary metering mechanism 22 and the secondary metering mechanism 42 travel among a number of stations of the analyzer 10. Each of these stations is defined as a metering stopping point for the metering truck 30 and 44 respectively. By way of example, and in no paticular order of significance or priority, these metering stopping points include for example: a primary metering point (P1) for the initial aspiration of sample by the primary metering mechanism 22; a reflex metering point (P2) where additional aspirates of sample can be taken if needed, i.e. for dilution purposes, etc.; a priority handling or STAT metering point (P3) for introducing priority/STAT samples; a thin film metering point (P4) where the slide element 36 is spotted with sample fluid; a tip seal point (P5) for sealing a lower end 105 of a metering tip 102 at the tip sealer 142 for forming a cuvette ("cuvetip"); a first tip pick-up point (P6) where the primary metering mechanism 22 obtains a new metering tip 102; a first tip eject point (P7) where the primary metering mechanism 22 drops off a used metering tip 102 or sealed tip 102 after testing has been completed; a second cuvette metering point (P8) where the secondary metering mechanism 42 meters samples from a cuvetip; a second tip pick-up point (P9) where the primary metering mechanism 22 obtains another new metering tip 102; a cuvette metering point (P10) where the secondary metering system meters into a wet cuvette (traditional type); a micro-tip pick-up point (P11) where the secondary metering mechanism 42 picks up new microtips (not shown); a second tip eject point (P12) where the secondary metering mechanism 42 deposits used microtips; and a wet reagent metering point (P13) where the secondary metering mechanism 42 aspirates wet reagent at the reagent wheel 52.

As will be described in greater detail later in the disclosure, these stations or points (P1–P13) are illustrative of the various points interacted on by the metering mechanisms 22 and 42 respectively. And, accordingly, the present invention is directed to a novel method of system calibration and automatic alignment of the metering mechanisms 22 and 42 using these pre-determined stations or points (P1–P13) of the analyzer 10.

Still referring to FIG. 1, a sample aliquot handler apparatus 40 is disposed in spaced relation between the first incubator assembly 34 of the dry chemistry system and the second incubator assembly 56 of the wet chemistry system of the above-described analyzer 10. The following discussion pertains to a specific description of the sample aliquot handler 40 followed by the operational details of the sample handler in conjunction with the wet and dry chemistry systems of the herein described combinational analyzer 10.

First, and as shown in FIGS. 1–3 and 5, the sample aliquot handler 40 includes a circular cylindrical housing 80 having a cover 84. The housing is defined by an interior sized for containing a number of retained components which include an inner rotor assembly 88 (not shown in FIG. 2) a pair of position sensors 126, 128, and a tip removing assembly 122. Each of the above-noted components are attached to an interior facing surface of a bottom mounting plate 138 of the housing 80. In addition, an outer rotor assembly 92 is supported at the top of the housing 80, the outer rotor assembly being disposed outside the periphery of the cover 84.

Figure 3:
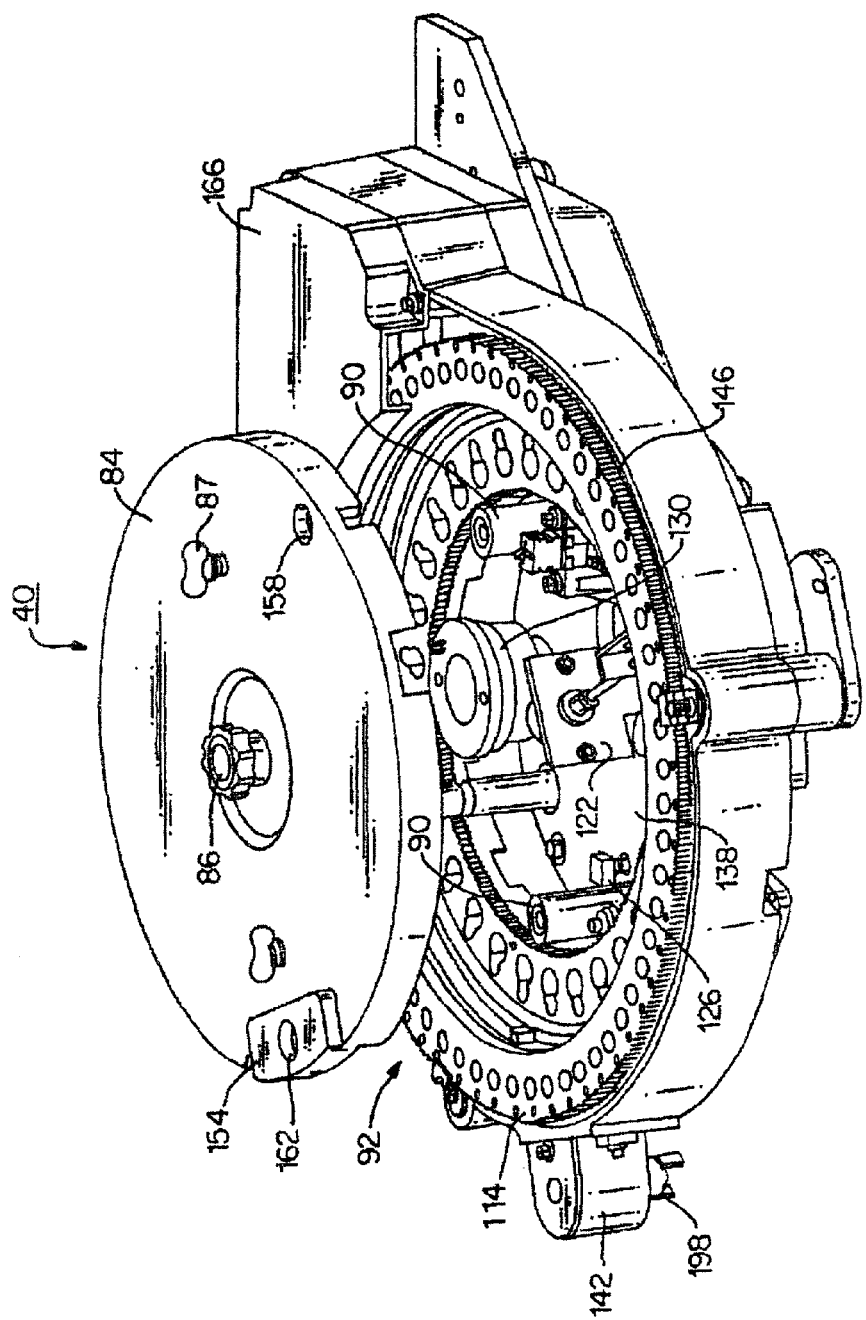
FIG. 3 is a partially exploded top perspective view of the sample aliquot handler of FIGS. 1 and 2.
Figure 4:
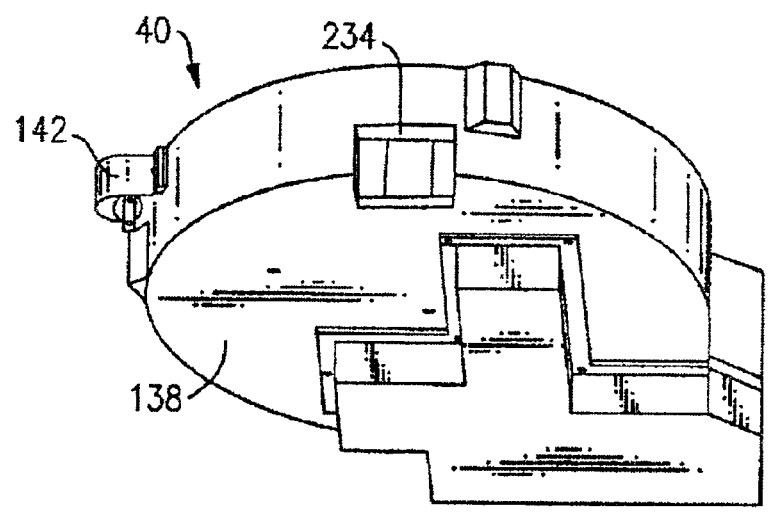
FIG. 4 is a bottom view of the sample aliquot handler of FIGS. 1–3.
Figure 5:
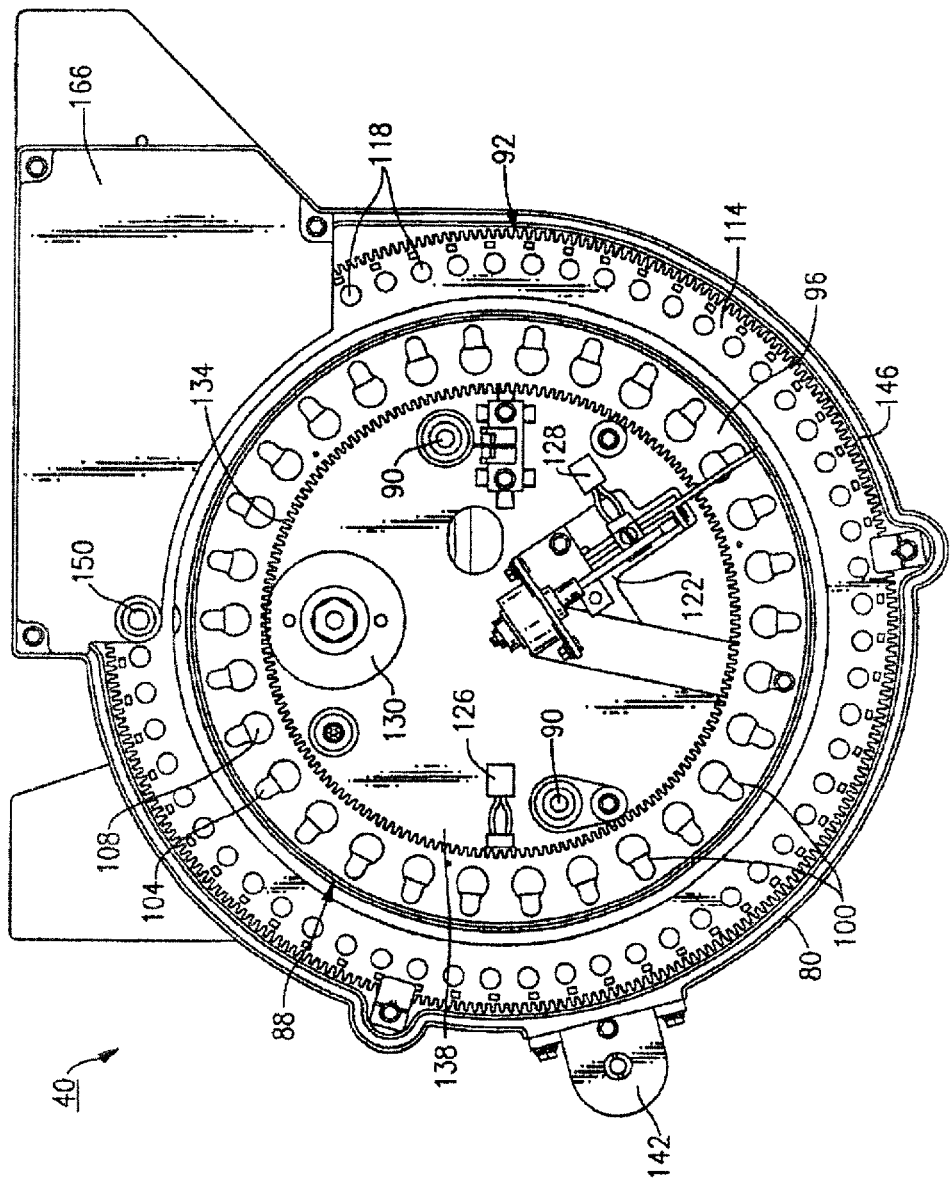
FIG. 5 is a top plan view of the sample aliquot handler of FIGS. 1–4.
Figure 8:
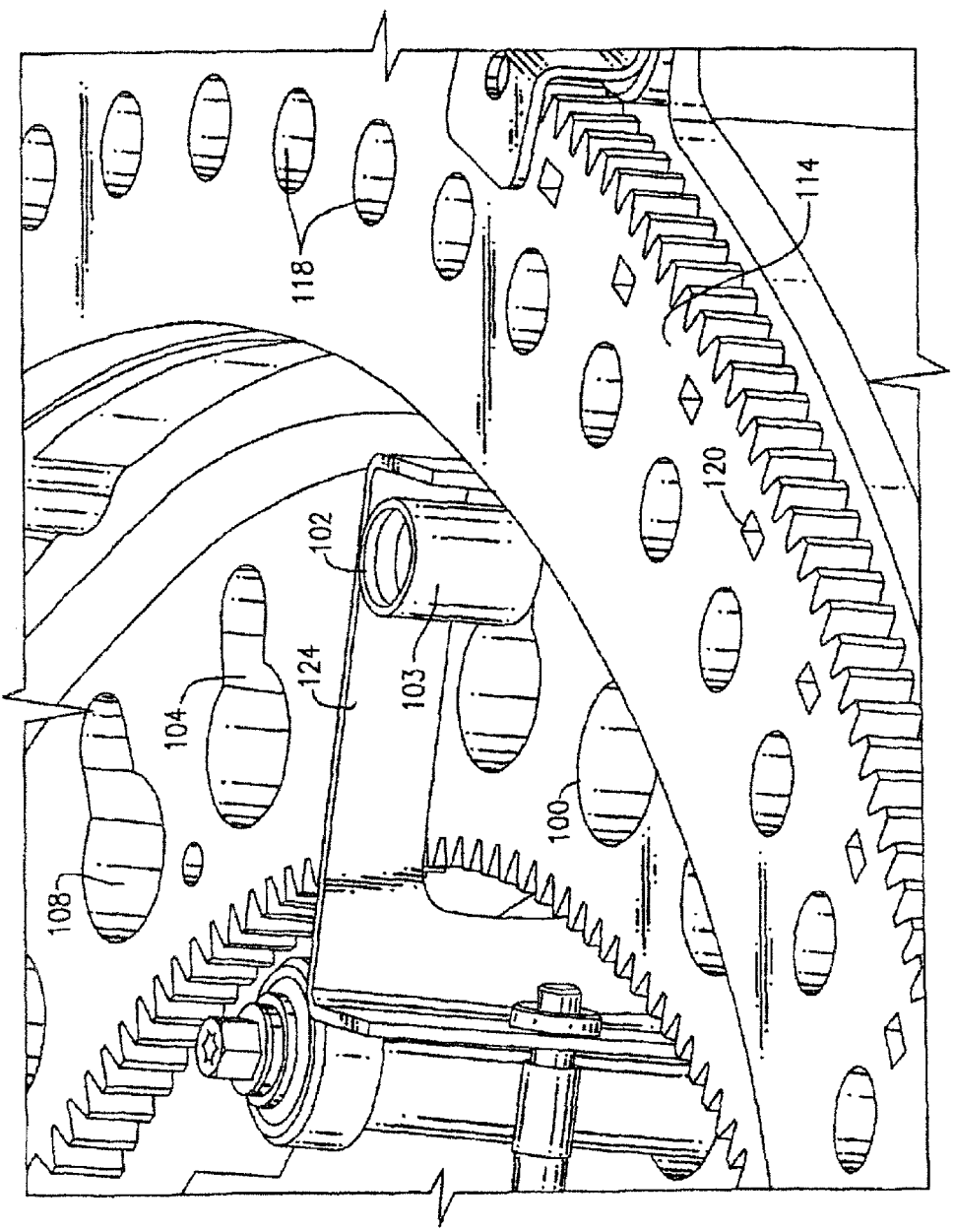
FIG. 8 is an enlarged partial top perspective view of the sample aliquot handler of FIGS. 1–7 showing the removal of a sealed metering tip from the handler to a dump station.

A pair of stanchions 90 also extending from the interior facing surface of the mounting plate 138 assist in supporting the cover 84 which covers the inner rotor assembly 88. The cover 84 further includes a center handle 86, as well as a pair of opposing twist fasteners 87 which engage corresponding openings provided in the stanchions 90. The cover to 84 also includes a tip stripping assembly 154 that is described in greater detail below. The following relates to a more detailed discussion of the inner and outer rotor assemblies 88, 92. Referring to FIGS. 3, 5, and 8, the inner rotor assembly 88 includes a rotatable circular ring member 96, which is rotatably driven about a center axis of rotation by means of a gear drive mechanism. The drive mechanism includes a motor having a rotating engagement portion 130 which extends above the interior facing surface of the mounting plate 138. A set of linear gear teeth 134 are provided on an inner edge of the ring member 96 which mesh with the engagement portion 130. The ring member 96 of the inner rotor assembly 88 further includes a plurality of sample container supply stations 100, each of the stations being circumferentially disposed about the periphery of the ring member. Each of the sample container supply stations 100 are defined by a slotted outer opening 104 which is linked to a radially adjacent and contiguous inner opening 108. The size of the inner opening 108 is much larger than that of the slotted outer opening 104 for reasons which will be become apparent below. According to this specific embodiment, (30) thirty sample container supply stations 100 are provided on the inner ring member 96, though it should be readily apparent that this parameter can be easily varied.

Referring now to FIGS. 2, 3, 5, and 8, and as noted above, the outer rotor assembly 92 of the sample aliquot handler 40 extends outside the periphery of the cover 84. This assembly is comprised of a circular support ring 114 having a plurality of circular circumferentially disposed tip supply stations 118 which are equally spaced about the periphery of the ring. Like the inner rotor assembly 88, a gear drive mechanism is used to rotatably drive the ring. A set of linear gear teeth 146 provided on an outer edge of the support ring 114 are engaged by the engagement portion (not shown) of a motor (not shown) to cause rotation of the support ring 114. It should be pointed out that the above described gear drive mechanisms are exemplary. That is, other drive mechanisms can be employed to cause rotational movement of either the support ring 114 or the ring member 96.

The support ring 114 and the ring member 96 of the outer rotor assembly 92 and inner rotor assembly 88, respectively, are concentric, the rotating components of each assembly being independently driven by their respective gear drive mechanisms about a common axis of rotation.

According to this embodiment, the support ring 114 of the outer rotor assembly 92 further includes a series of circumferentially spaced slots 120, FIG. 8, disposed on an outer periphery of the ring for aiding in the initial angular positioning of the ring during assembly.

Figure 9:
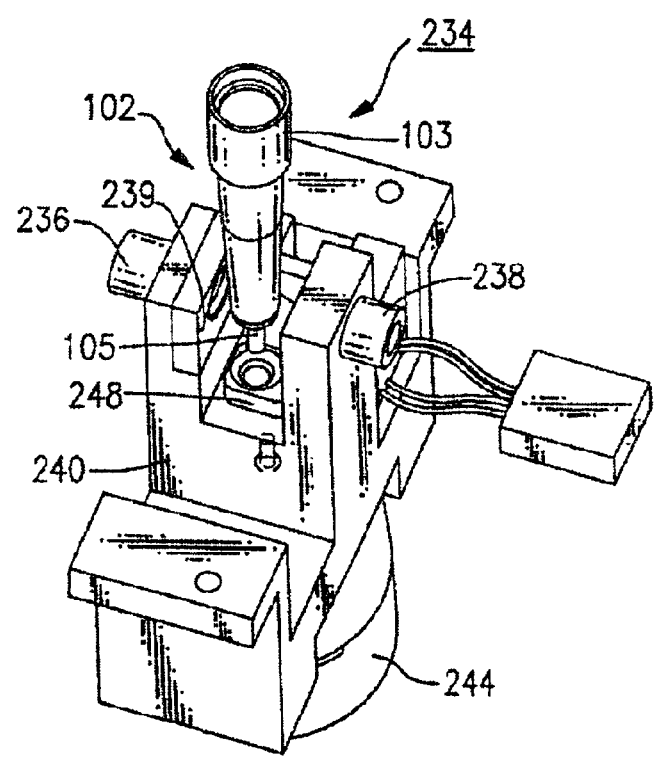
FIGS. 9 and 10 are partial side elevational views illustrating an sample integrity read station in accordance with one embodiment of the invention for the sample aliquot handler of FIGS. 1–8.

Still referring to FIGS. 2, 3, 5 and 8, each of the tip supply stations 118 of the support ring 114 of the outer rotor assembly 92 are circular openings which are sized to receive a metering tip 102, FIG. 9, 10, from a tip supply (not shown) at a tip deposit station 150 provided as an opening in an adjacent cover 166 covering the drive motor (not shown) for the rotatable support ring 114 of the outer rotor assembly 92. According to this embodiment, a total of sixty (60) equally spaced tip supply stations 118 are provided, though it should be apparent, as previously noted above, that this parameter can be suitably varied.

According to this specific embodiment, each of the sample container supply stations 100 and the tip supply stations 118 of the inner rotor and outer rotor assemblies 88, 92, respectively, are sized to receive a fluid aspirating/dispensing member. According to this embodiment, the fluid aspirating/dispensing member is a metering tip 102, shown in FIGS. 9 and 10, which includes an open upper end 103 and a lower dispense end 105 through which liquid can be dispensed. More specifically, the metering tip described herein is a disposable plastic member manufactured by the Johnson & Johnson Company under the trade name of Vitros™, though it will be apparent that other fluid dispensing/aspirating members can be substituted.

Referring to FIGS. 2–6, the sample aliquot handler 40 includes a tip sealer 142 which is mounted by conventional means, such as threaded fasteners, to the exterior of the housing 80.

Figure 6:
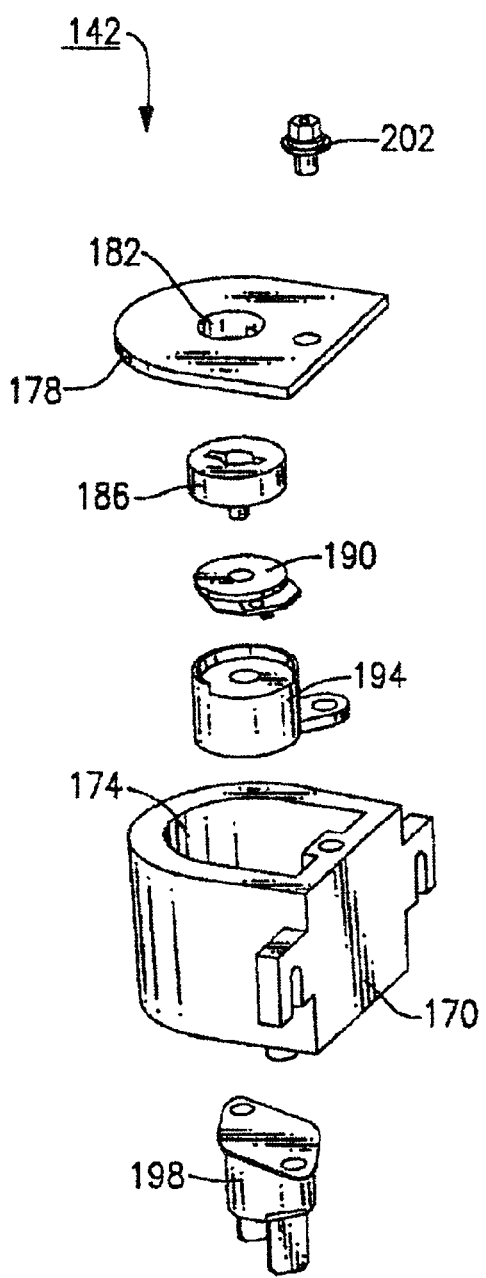
FIG. 6 is an exploded top perspective view of a tip sealer used in connection with the sample aliquot handler of FIGS. 1–5.

Referring more particularly to FIG. 6, the tip sealer 142 includes a housing 170 which is mounted to the exterior of the handler housing 80, FIG. 3, the housing having a defined interior 174 and a cover 178 which covers the top end of the housing. A number of components are contained within the sealer housing 170 including a cylindrical support 194, and a heating element assembly 190, which is placed in a recess of the support within a bottom portion of an anvil 186. The heating element assembly 190 includes a resistive type heater and a control thermistor. The cover 178 includes a center opening 182 which is sized to permit passage of a metering tip 102, FIG. 9, such that the opening of the dispense end 105 of the tip can be sealed through engagement with the heated anvil 186. A safety thermostat 198 attached to the bottom of the housing 170 automatically shuts down the tip sealer 142 if a predetermined temperature is reached to prevent overheating. Further details relating to the sealing of metering tips in this manner is described in commonly owned U.S. patent application Ser. No. 09/658,356 to Jacobs et al., entitled ANALYZER WITH SAMPLE QUALITY MEASUREMENT, AND METHOD, the entire contents of which are incorporated herein by reference.

Figure 7:
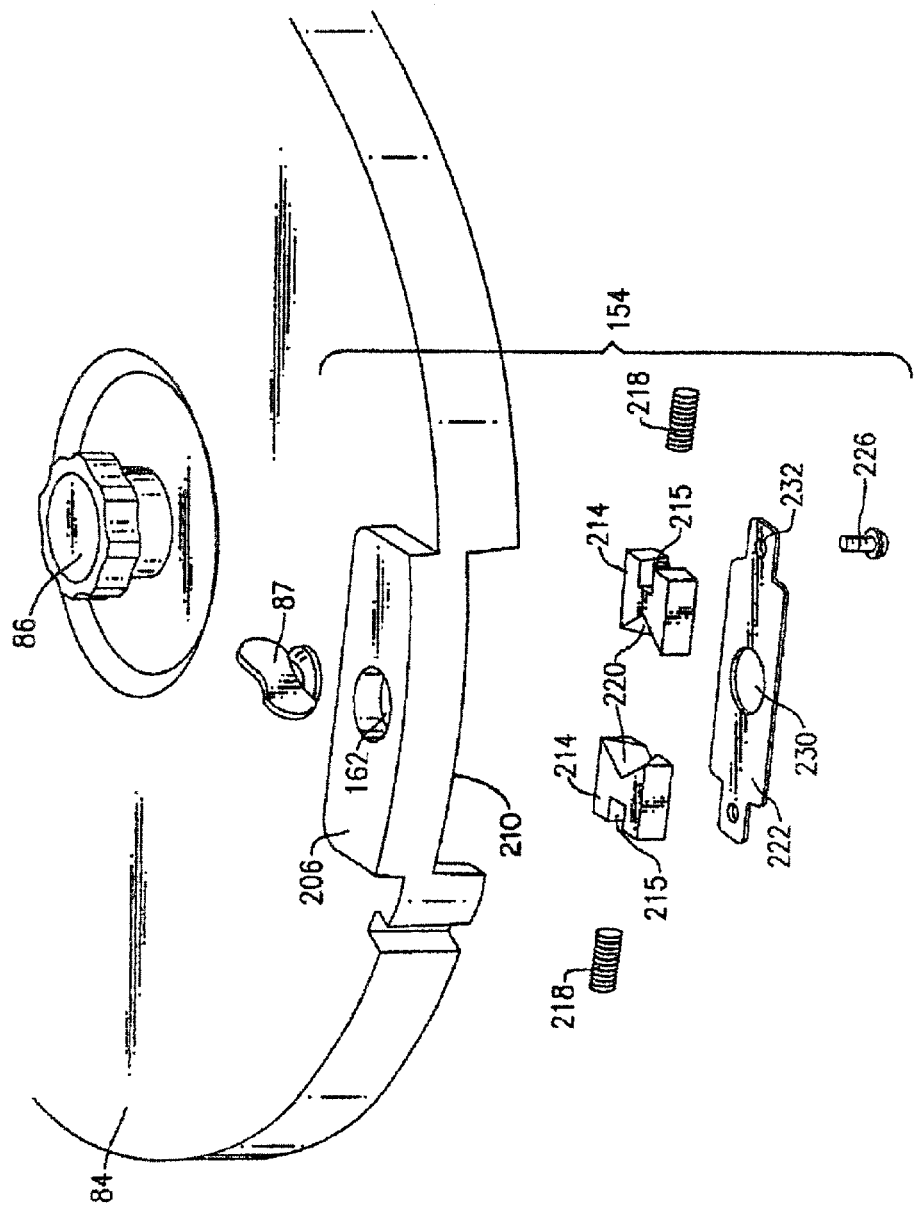
FIG. 7 is a partial top perspective of the cover of the sample aliquot handler of FIGS. 1–6 showing an exploded view of a tip stripper.

Referring to FIG. 7, the sample aliquot handler 40 further includes a tip stripping assembly 154 that is provided within a recessed portion 210 of the bottom of the cover 84. A pair of V-blocks 214 are biasedly maintained in a first or "home" position by a pair of compression springs 218 within respective slotted regions 215. The V-blocks 214 are biased in order to create a predetermined gap between a pair of tapered surfaces 220. The cover 84 includes an opening 162 within a raised portion 206, which is aligned with the gap of the V-blocks 214 to permit passage there through of a metering tip 102, FIG. 9. A retaining plate 222 used to support the components of the tip stripping assembly 154 is secured to the bottom of the cover 84 using fasteners 226 (only one being shown in FIG. 7) which extend through corresponding holes 232 formed in the retaining plate.

Figure 10:
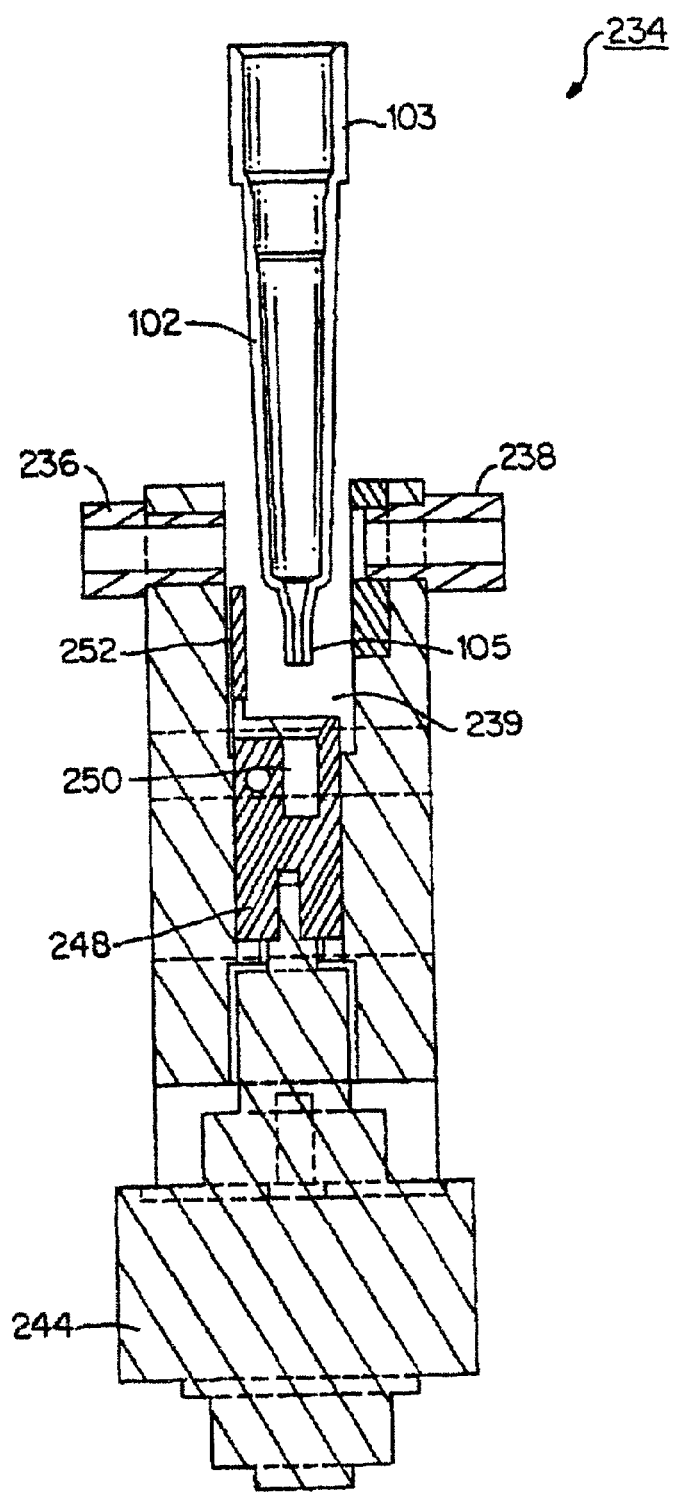

Referring to FIGS. 9 and 10, a sample integrity read station 234 includes a station housing 240 and an optical reading device, such as a spectrophotometer which includes receiving and transmitting optics 236, 238 disposed on opposite sides of a test slot or cavity 239. A linear actuator 244 is disposed at the bottom of the station housing 240, the actuator having an engagement member 248 attached thereto which is vertically movable and includes a tip receiving cavity 250 and a vertically extending flag 252, according to this embodiment. The actuator 244 and engagement member 248 together form a lift mechanism that aligns the fluid contents of a retained metering tip 102 with the receiving and transmitting optics 236, 238 of the spectrophotometer. The housing 240 of the sample integrity read station 234 is stationarily positioned to the mounting plate 138 beneath a predetermined angular position of the circular ring 96 and the cavity 239 is aligned with the sample container supply stations 100, FIG. 5. As described below, the sample integrity received station 234 is provided to provide spectrophotometric analysis of the sample contents of a sealed metering tip 102 in order to ascertain the presence of certain sera components, such as hemoglobin, albumin, lipoproteins etc.

As will now be more clearly described, the above-described sample aliquot handler 40 is used to asynchronously link the dry chemistry and wet chemistry systems of the combinational clinical analyzer 10. Having completed the description of the individual features and subassemblies of the sample aliquot handler 40, details relating to the operation of the sample handler in terms of the analyzer 10 is now provided.

Initially, a plurality of unsealed metering tips 102 are loaded one at a time as fed from a tip supply (not shown) through the opening that defines the tip deposit station 150 and are dropped into empty tip supply stations 118 provided on the support ring 114 of the outer rotor assembly 92. The support ring 114 is rotated incrementally by means of the gear drive mechanism (not shown) in order to align empty tip supply stations 118 into proper alignment with the tip deposit station 150.

As previously noted, the primary sample handler 14 contains a plurality of patient sample containers 18 which are movably disposed on a carousel. Details relating to the primary sample handler 14 and movement of the sample containers 18 are commonly known to those of ordinary skill in the field and do not form an essential part of the invention. As noted above, the metering transport rail 26 is aligned with the primary sample handler 14 and the auxiliary sample handler 40 such that a metering tip 102, FIG. 9, can be attached onto a proboscis (not shown) of the movable metering truck 30 of the primary metering mechanism 22 from a predetermined tip supply station 118.

The metering truck 30 is then shuttled along the transport rail 26 to the primary sample handler 14 and a volume of sample is drawn under vacuum and is aspirated from one of the patient sample containers 18 into the metering tip 102, FIGS. 9 and 10. Specific details relating to the attachment of a metering tip to a proboscis as well as details relating to the aspiration and metering of sample and other fluids are commonly known to those in the field. An example is provided, for example, in U.S. Pat. No. 4,340,390 to Collins et al., the entire contents of which are herein incorporated by reference.

Figure 11:
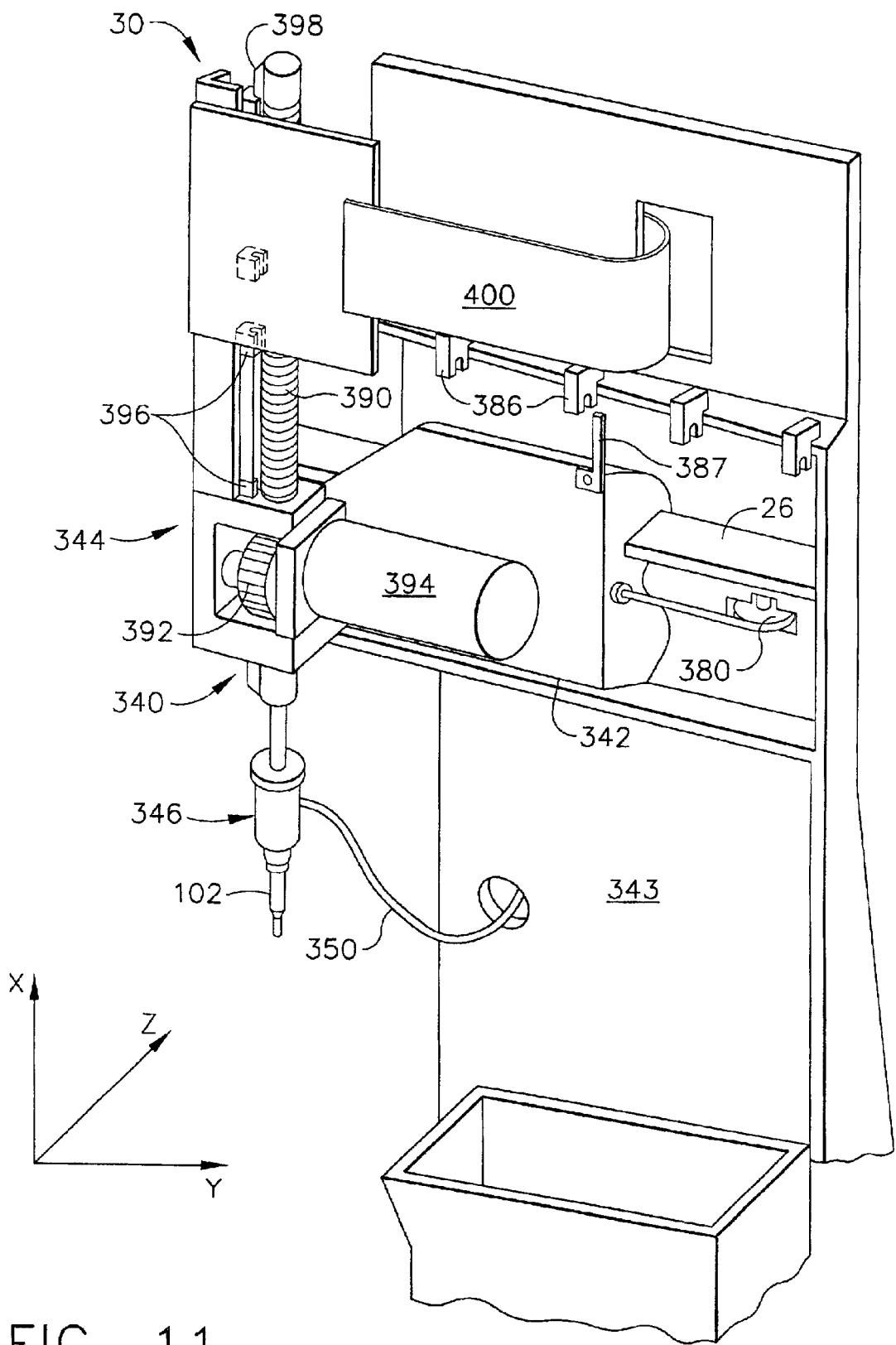
FIG. 11 is a perspective view of a metering system for the analyzer of FIG. 1 showing a dispenser and a carriage.

With reference to FIG. 11, metering truck 30, 44 comprises a dispenser 340 and a means for positioning dispenser 340 which includes a carriage 342 for moving dispenser 340 laterally through a plurality of stations (P1 through P13 as shown in FIG. 1) in analyzer 10, and a vertical drive 344 for raising and lowering dispenser 340 at each of the stations P1 through P13. Dispenser 340 comprises a dispenser head 346 which is adapted to receive disposable metering tip 102, and is connected by means of a line 350 to a pump 352 (FIG. 12) of the positive displacement type. Pump 352 comprises a piston, not shown, which is driven by a bi-directional stepper motor 354. The stepper motor 354 is operatively connected to and controlled by a control system 410.

When motor 354 is actuated by the control system 410 in one direction, a partial vacuum is created in line 350 by pump 352, and fluid is drawn into tip 102 until the tip is partially filled. Motor 354 is actuated in an opposite direction to meter fluid from tip 102. In the metering operation, motor 354 drives pump 352 for a pre-selected period during which the pressure in line 350 and tip 102 is raised sufficiently to force about 10 ul of fluid onto an analysis slide. Under certain operating conditions, depending on the amount of fluid aspirated into tip 102, it may be desirable to vent line 350 before dispensing fluid onto an analysis slide. A pressure transducer 356 is operatively connected to and controlled by control system 410 and closely monitors pressure in line 350 for purposes which will be explained in more detail hereinafter.

Carriage 342 is mounted for horizontal movement on metering transport rail 26. Rail 26 is carried on a pylon 343 attached to the analyzer frame, not shown. A drive means for carriage 342 includes a bi-directional stepper motor 372 (FIG. 12) which is connected to a capstan drive 374. Drive 374 comprises a drum 376; a cable 378 carried on drum 376 is supported on guide pulleys 380 and connected to carriage 342. The stepper motor 372 is operatively connected to and controlled by the controller 410. It will be seen from FIGS. 11 and 12, that when motor 372 is driven, for example, in a counterclockwise direction, as viewed in FIG. 12, carriage 342 will move to the right (FIG. 11). Carriage 342 must be located along a line at multiple points or stations which include for example, stations at positions P1 through P13. Horizontal-position sensors 386 of a photoelectric type cooperate with a carriage flag 387 on carriage 342 to precisely position the carriage 342 at each of these stations P1 through P13.

Vertical drive 344 comprises a rack 390 which is attached to dispenser head 346. Rack 390 is raised and lowered by means of a pinion 392 driven by a stepper motor 394 mounted on a carriage 342. Vertical-position sensors 396 cooperate with a rack flag 398 on rack 390 to precisely determine the vertical position of dispenser head 346. Power from a power supply, not shown, is supplied to the sensors 396 and motor 394 through a ribbon cable 400. The sensors 396 and motor 394 are operatively connected to and controlled by the controller 410 through the ribbon cable 400.

In the use of the disclosed metering mechanism 22 and 42 with the high-throughput clinical analyzer 10, as shown in FIG. 1, a metering operation takes place approximately every nine (9) seconds. Thus, it will be seen that each of the steps in the metering cycle must be carefully controlled and monitored by the control system 410, and metering apparatus 30 and 44 must function in timed relation to other elements of analyzer 10. Pressure transducer 356 is used to monitor the performance of apparatus 30 and 44. Pressure is sensed in line 350, and if conditions are present such as a plugged tip 102, no fluid in sample container 18, or a separation of the fluid stream between the tip 102 and the slide element 36, or if the tip 102 is close to a surface, they will be detected by the pressure transducer 356. The control system 410 for the metering apparatus 30 and 44 includes one or more computers which may take any of the various forms known in the art that include programmable microcomputers. In general, the instructions and method of programming such computers is well known in the art, and thus, no further explanation is considered necessary. However, as will be described in detail later in that disclosure, the control system 410 includes a novel algorithm that is used for the novel method of calibration and novel automatic alignment method for the analyzer 10.

The metering truck 30 carrying the unsealed metering tip 102 with aspirated sample is shuttled along the transport rail 26 from the primary sample handler 14 to the metering station 68. At the metering station 68, a volumetric portion of patient sample contained within the metering tip 102 is dispensed onto a dry slide element, shown pictorially as 36 in FIG. 1, which is arranged to be loaded using conventional means, such as a reciprocating pusher blade 39, also shown pictorially in FIG. 1, into the first incubator assembly 34. The sample which is metered is then used in conjunction with the dry chemistry system of the herein described combinational analyzer 10. The sample is metered onto, for example, a colorimetric or potentiometric slide element which is incubated, the sample being analyzed at a read station for correlated analyte detection. Details relating to the incubation and testing of dry slide elements is known in the field such as described, for example, in U.S. Pat. No. 4,296,069 entitled: Apparatus for Processing an Analysis Slide, and therefore require no further discussion.

Following the above-described metering step, the metering tip 102 is then further shuttled by the metering truck 30 toward the sample aliquot handler 40 and more specifically to the tip sealer 142. At the tip sealer 142, the metering tip 102 is placed within the opening 182 of the sealer housing 174 and is lowered until the tip is positioned relative to the anvil 186. Heat from the heating element 190 is applied through the anvil 186 to the dispense end 105 of the tip 102 while the tip is still attached to the proboscis (not shown) of the metering truck 30. The fluid within the tip 102 is aspirated further away from the dispense end 105 and a bubble is formed which prevents temperature effects to the fluid as well as removing the fluid from the area to be sealed. As noted above, further details relating to the above noted sealing operation are provided in previously incorporated U.S. patent application Ser. No. 09/658,356 entitled: ANALYZER WITH SAMPLE QUALITY MEASUREMENT, AND METHOD.

The above sealing operation seals the dispense end 105 of the metering tip 102, FIGS. 9, 10, and therefore creates a sample supply container for use by the wet chemistry system of the present combinational analyzer 10 as will be described below.

Following the above sealing steps, the proboscis (not shown) is raised in a conventional manner, removing the metering tip 102 from the tip sealer 142. The metering tip 102 is then shuttled along the transport rail 26 by the metering truck 30 to the tip stripping assembly 154 which is provided on the cover 84 of the sample aliquot handler 40. The opening 162 of the tip stripping assembly 154 is aligned with the transport rail 26 and more specifically the travel path of the metering truck 30. The proboscis (not shown) is lowered along with the attached metering tip 102, FIG. 9, into the opening 162 of the raised portion 206 of the cover 84. Initially, the dispense end 105 of the sealed metering tip 102, FIGS. 9, 10, engages the ramped surfaces 220 of the V-blocks 214. As the proboscis is further lowered, the downward force applied by the tip 102 against the ramped surfaces 220 causes the gap between the V-blocks to widen and permits the entire metering tip 102 to pass through the extended gap. When the top of the upper end 103 of the metering tip 102 has passed through the V-blocks 214, the V-blocks are caused to close inwardly due to the biasing force applied by each of the compression springs 218 toward the body of the proboscis, above the top of the metering tip 102. Upward movement of the proboscis therefore causes engagement against the shoulder of the open upper end 103 of the metering tip 102, causing the tip to be stripped from the proboscis and dropped into an empty sample container supply position 100 of the circular ring 96 of the inner rotor assembly 88.

A tip presence sensor located at a dump position of the sample aliquot handler 40 indicates whether or not a sample container supply station 100 is empty prior to loading the sealed metering tip 102, the sensor further confirming the presence of a new tip which has been loaded.

The above noted steps are repeated in order that a plurality of sealed metering tips 102 are individually added to the sample aliquot handler 40 and more specifically to sample container supply stations 100 of the inner rotor assembly 88. The rotatable ring 96 of the inner rotor assembly 88 is driven about its axis of rotation through means of the meshing of the engagement portion 130 of the drive motor and the gear teeth 134 provided on the ring 96 either incrementally or as required. The retained sample containers (sealed metering tips 102) are driven relative to an aspiration station 158 and sample integrity read station 234. According to the present embodiment, the sample integrity read station is angularly disposed between the tip stripping assembly 154 and the aspiration station 158. The locations of each of the above stations 158, 234 can of course be suitably varied. What should be noted is that the disposition of the sample integrity station 234 within the housing of the sample aliquot handler 40 permits readings to be performed at a time which does not affect throughput of the analyzer 10.

As more clearly shown in FIGS. 9 and 10, a sealed metering tip 102 is advanced by the inner rotor assembly 88, FIG. 3, to the sample integrity station 234. As noted previously, the A sample integrity read station 234 is placed at a predetermined circumferential position relative to the sample container supply positions 100 of the rotatable ring 96. At this station 234 and according to his embodiment, the sealed metering tip 102 is roughly angularly aligned with the test cavity 239 and moreover is roughly vertically aligned with the receiving and transmitting optics 236, 238 of the optical testing device in the position which is shown in FIG. 10.

The optical reading apparatus according to this embodiment, is a spectrophotometer which makes light absorbance transmission measurements of a sample retained within the sealed disposable metering tip 102. The sealed metering tip 102, being made from a transparent plastic material therefore permits optical testing to be performed upon the fluid contents. Details relating to the optical reading of the fluid contents of the sample are known as provided in U.S. Pat. Nos. 6,013,528 and 5,846,492, to Jacobs et al., the entire contents of each being hereby incorporated by reference.

According to this embodiment, the lift mechanism is used to better or repeatably align each sealed metering tip 102 to the receiving and transmitting optics 236, 238 of the optical testing apparatus. The actuator 244 is initially engaged and the tip receiving cavity 250 of the engagement member 248 of the linear actuator 244, sized to receive the dispense end 105 of the tip 102, causes the tip to be moved upwardly relative to its position within the ring 96 (the ring is not shown in FIGS. 9 and 10). The upward movement of the sealed metering tip places the lower portion of the tip containing the aliquot of sample fluid into proper alignment between the receiving and transmitting portions 236, 238 of the optical testing device prior to obtaining readings of the contained aliquot sample. The flag 252 provided on the engagement member 248 is used to perform a dark read of the optical reading apparatus prior to lifting the metering tip 102, as better described by the above incorporated Jacobs patents.

Upon completion of the read, the engagement member 248 is lowered and the metering tip is again lowered into engagement within the outer slotted opening 104 of the corresponding sample container supply position 100. The ring 96 of the inner rotor assembly 88 resumes rotational movement by means of its gear drive mechanism until the metering tip 102 is aligned with the opening representing the aspiration station 158. If sample is required, the secondary metering system 42 is used to bring a micro-tip (not shown) from the micro-tip loader 58 using a proboscis (not shown) extending downwardly from the movable metering truck 44 which is moved into position using the metering transport rail 26. The operation of the secondary metering mechanism in terms of the attachment of a tip to the proboscis (not shown), the raising and lowering of the proboscis relative to the metering truck 44, the movement of the metering truck along the transport rail 26 and the aspiration and dispensing of fluid using the micro-tip are literally identical to that of the primary metering mechanism 22, FIG. 1 and those details in and of themselves require no further discussion. As previously defined, however, the micro-tip is a fluid dispensing member which can fit within the confines of a sealed metering tip 102.

The micro-tip is positioned within the confines of the sealed metering tip 102 in order to aspirate a predetermined volume of liquid from the sealed tip to use the liquid to conduct a wet assay or dilution. The metering truck 44 then moves the micro tip into alignment with a reaction vessel 64 and dispenses the aspirated fluid. Following the delivery of patient sample aspirated from the secondary sample container, the micro tip is disposed of by dropping the used micro-tip into a dump station (not shown) of the analyzer 10.

According to this embodiment, separate liquids, such as at least one reagent fluid, are also brought to the reaction vessel 64, from the reagent wheel 52 using a separate metering tip 102, FIG. 9 which aspirates fluid from a container disposed within the reaction wheel and dispenses the reagent fluid as needed. For example, reagent (s) can be aspirated using a tip 102 which is obtained by the secondary metering mechanism 42 from the outer rotor assembly 92. Preferably, the coordination of wet assay testing utilizes the sample aliquot handler 40 as part of the scheduling in order to effectively utilize throughput. Details relating to the operation of the wet chemistry portion of the herein described analyzer are provided in concurrently U.S. patent application Ser. No. 09/910,399 filed on Jul. 20, 2001 entitled: "Chemistry System for a Clinical Analyzer" to Jakubowicz et al., the entire contents of which are herein incorporated.

Once the sealed metering tip 102 has been used in accordance with all tests/assays which may be required based on the scheduling of the combinational analyzer 10, the ring 96 of the inner rotor assembly 88 is rotated into alignment with the tip removal assembly 122. At this location, an actuable hook blade 124 which is moved outwardly by the assembly engages the protruding upper end 103 and body of the metering tip 102 and pulls the tip from the slotted outer opening 104 of the supply station 100 to the larger diameter inner opening 108. The inner opening 108 of the sample container supply stations 100 has a diameter which is larger than that of the upper end 103 of the tapered metering tip 102, thereby causing the tip to fall through the opening and into a dump station (not shown) located beneath the ring 96. A position sensor 128 detects the position of the hook blade relative to the inner rotor assembly 88.

Calibration & Automatic Alignment Method

For purposes of the remainder of this disclosure, the terms "dispenser", "metering system", "metering apparatus", "metering mechanism", and "metering truck", are defined as either the primary metering mechanism 22 and/or the secondary metering mechanism 42 to include the metering trucks 30 and 44 respectively.

Figure 12:
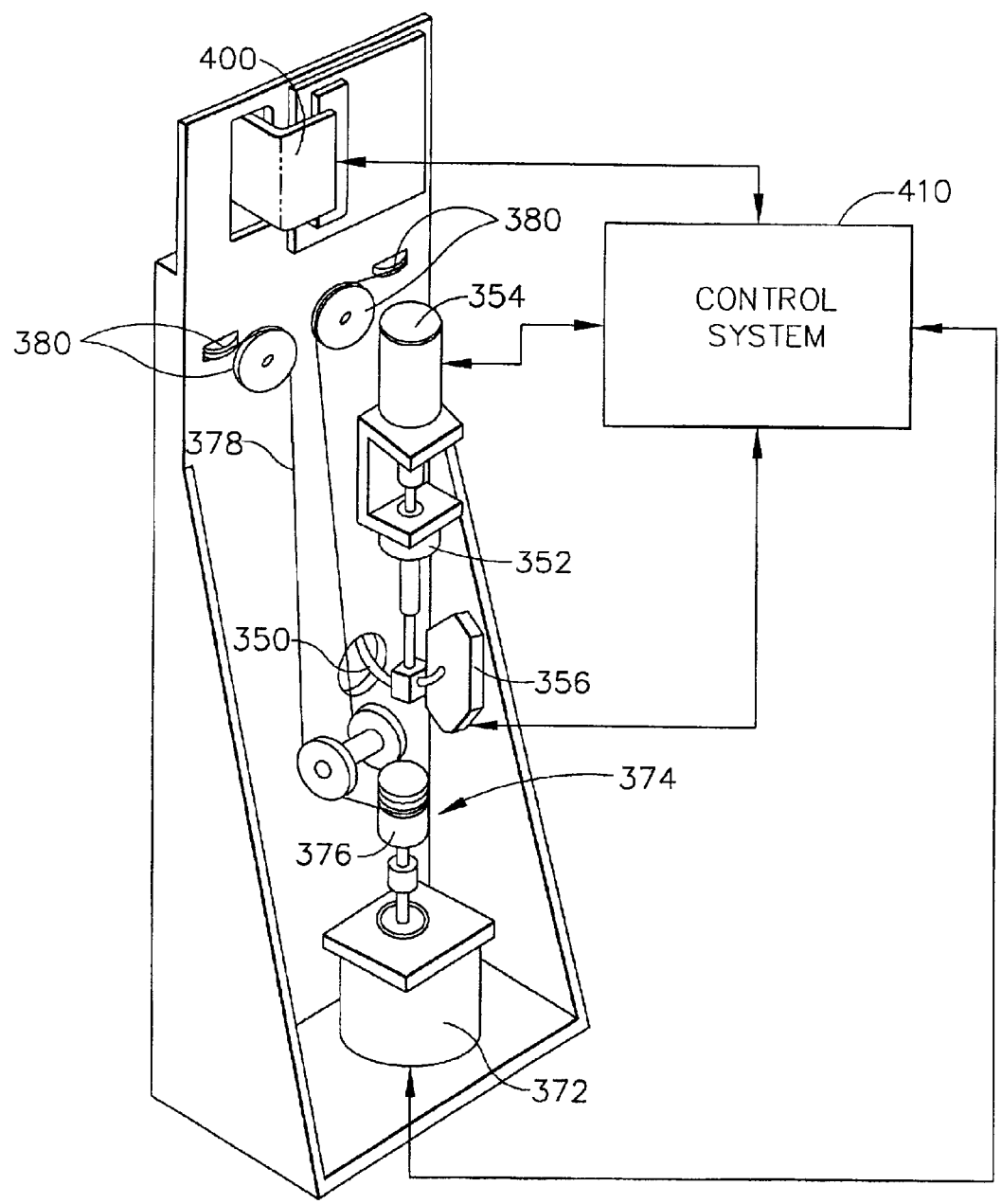
FIG. 12 is a perspective view of a pump for the dispenser and a drive mechanism for the carriage operatively connected to a control system for performing a calibration and automatic alignment method in accordance with the present invention.

In utilizing the calibration and automatic alignment method for the clinical analyzer in accordance with the present invention, the metering system 30, 44 utilizes a pressure level sensing approach, as illustrated in FIGS. 11 and 12, as a pressure monitoring device for sensing the level of fluid in sample container 18 (FIG. 1), reagent container, test tube, Eppendorf tube, or any other component capable of having a fixed or variable level of medium contained therein.

As shown in FIGS. 11 and 12, the metering system 30 and 44 utilizes pump 352 to force air through line 350 and ultimately through the metering tip 102. Additionally, as air is forced out of the metering tip 102, the metering tip 102 is slowly lowered to the sample container 18 or one of the other containers such as those mentioned above or calibration element 19 (FIGS. 14A and 14B). Additionally, pressure transducer 356 senses whether there is back-pressure that forms within the metering tip 102 throughout the level sensing procedure. As the metering tip 102 approaches a particular height above the surface level of the fluid, back-pressure forms within the metering tip 102 wherein the pressure transducer 356 detects the pressure change. Detected pressure changes are monitored by the control system 410 through a feedback signal provided from the pressure transducer 356 to the control system 410. This back-pressure signal alerts the control system 410 that the metering tip 102 is close to the surface level of the fluid. Alternatively, in lieu of a pressure level sensing, capacitance level sensing can be utilized with the present invention. For instance, the dispenser 340 is comprised of a conducting material such as a metal or conductive polymer so that its body can be used to detect changes in capacitance and thus serve as a level sensor as is well known in the art.

The control system 410 is pre-programmed in order to automatically move the metering system 30 and 44 to any desired position on the clinical analyzer 10. For instance, control system 410 moves the metering system 30 and 44 in at least two or three dimensions such as orthogonal directions X, Y, and Z as shown in FIG. 11. The control system 410 controls movement of the metering system 30 and 44 in these distinct directions through direct operation and control of the motor 372 and the stepper motor 394.

Additionally, the level sensing approach identified above in accordance with the present invention is utilized for sensing and monitoring the distance of the metering system 30 and 44 to non-liquid surfaces. For instance, this level sensing technique can be used to sense height variations in various components of the clinical analyzer such as the incubator rings (not shown), etc.

Figure 13:
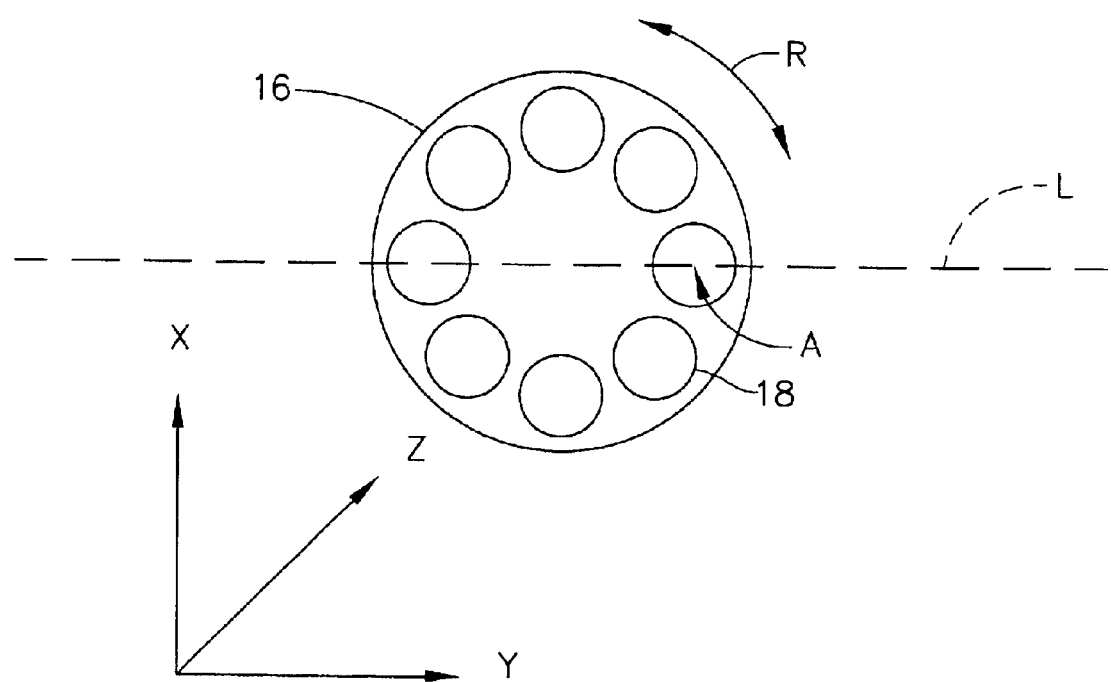
FIG. 13 is a schematic top view of a sample tray with sample containers for identifying an alignment point for the dispenser of FIG. 11.
Figure 14A:
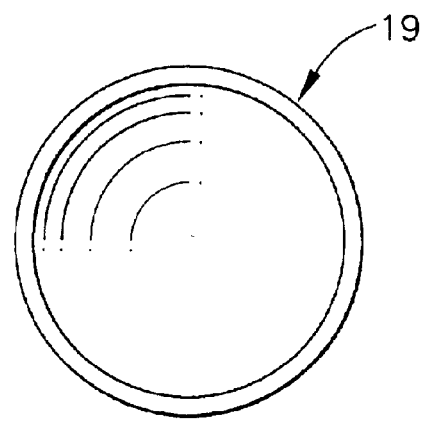
FIG. 14A is a schematic top view of a calibration element for the analyzer of FIG. 1 in accordance with the present invention.
Figure 14B:
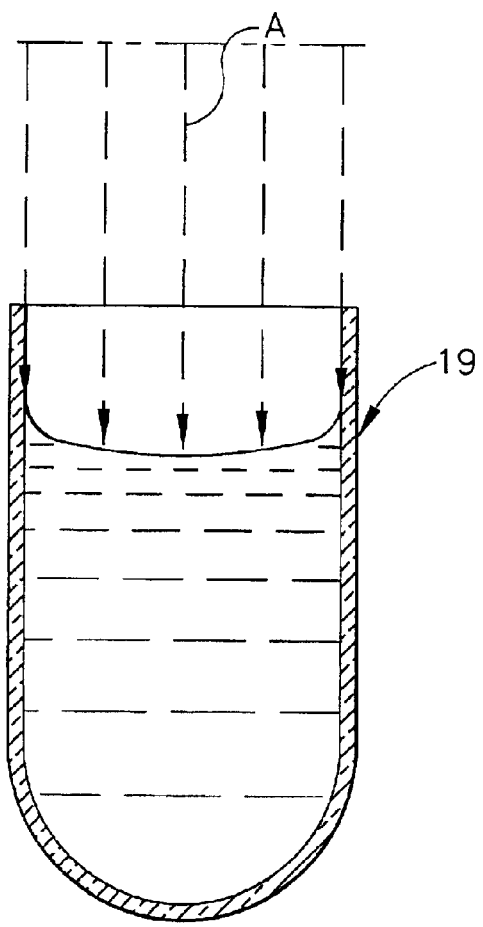
FIG. 14B is a schematic side view in cross-section of the calibration element of FIG. 14A.

As best shown in FIGS. 13, 14A and 14B, the analyzer 10 is calibrated by using a calibration element 19 (FIGS. 14A and 14B). The calibration element 19 has a fixed, solid surface and is in the form of any suitable component or container such as a test tube, sample container, reagent container, Eppendorf tube, or the like. Additionally, the calibration element 19 can take the form of other specific non-liquid holding components of the analyzer 10.

In conducting the calibration method in accordance with the present invention, the calibration element 19 is pre-positioned at each desired station or metering point for example points P1–P13 (FIG. 1) in order to provide an initial calibration procedure for the analyzer 10 through use of the metering system 22 and 42 (metering trucks 30 and 44). All calibration information determined from the calibration method in accordance with the present invention is stored in the memory (computer) of the control system 410.

Figure 15:
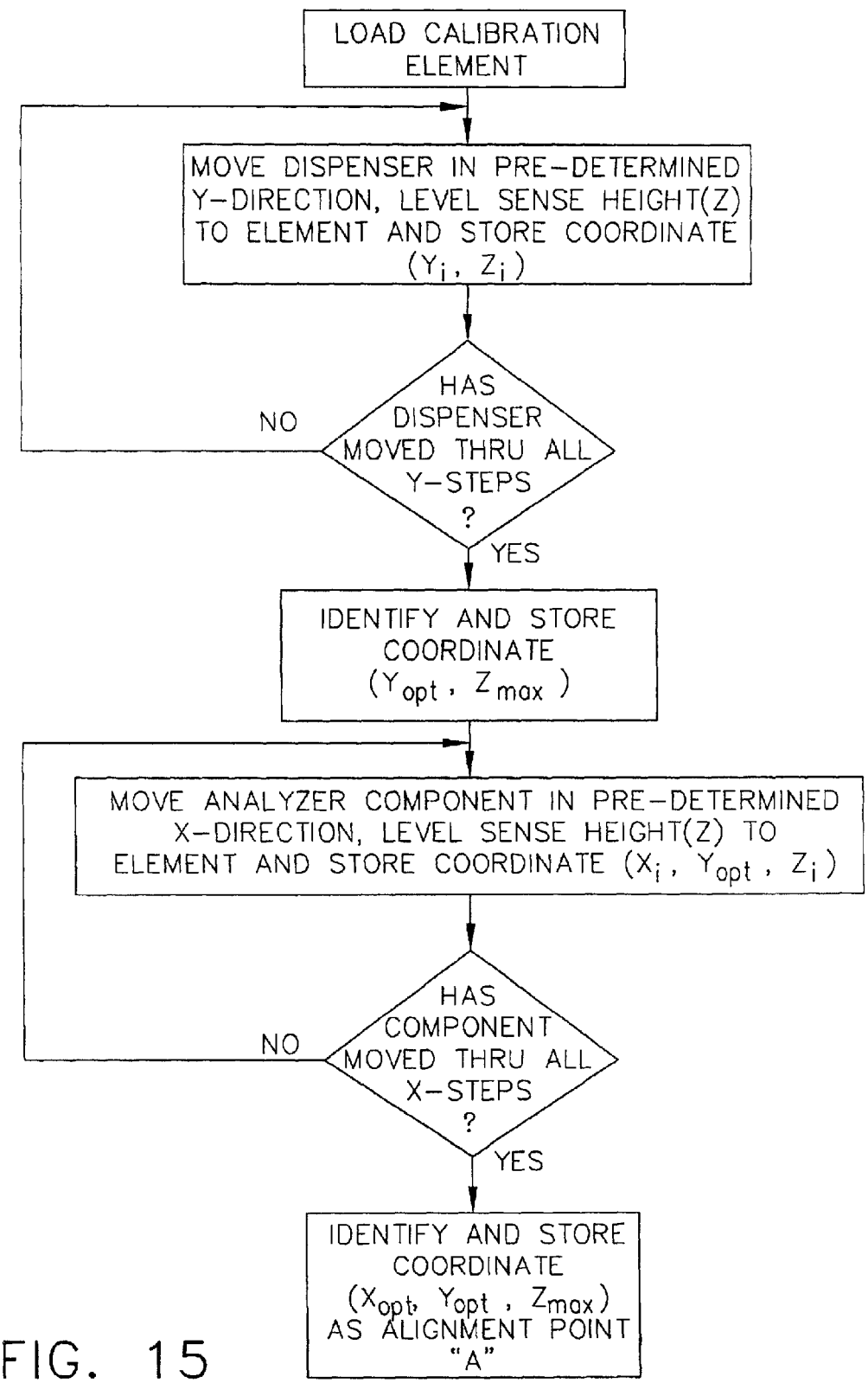
FIG. 15 is a block diagram illustrating a calibration algorithm and method for the dispenser of FIG. 11 in accordance with the present invention.

The algorithm for the calibration and automatic alignment method in accordance with the present invention is shown in FIG. 15. Accordingly, in performing the method according to the present invention, the calibration element 19 is loaded at a portion or specific location of the clinical analyzer 10 wherein the dispenser 340 of the metering system 30 and 44 is moved by the control system 410 to a pre-determined position over the calibration element. For example, the dispenser 340 is moved or stepped a pre-determined distance in the Y direction such that the dispenser 340 positions the metering tip 102 over the calibration element 19 (FIGS. 14A and 14B).

Once the dispenser 340 is moved in the pre-determined Y direction, the pressure level sensing technique described above is utilized such that air is forced out of the dispenser 340 through its metering tip 102 and back-pressure in the metering tip 102 and dispenser 340 is measured by the pressure transducer 356 and control system 410. As mentioned previously, back-pressure is converted to a signal that is sent from the pressure transducer 356 to the control system 410. This signal is converted and correlated to a level sense height (Z) which is the height or distance measured between the distal portion 105 of the metering tip 102 to the surface of the calibration element 19. At this point, the control system 410 identifies the two-dimensional position coordinate of the dispenser 340, for instance coordinate ($Y_i, Z_i$), wherein the coordinate ($Y_i, Z_i$) is stored in the memory of the control system 410. The control system 410 then moves or steps the dispenser 340 to the next pre-determined step or increment in the Y direction over the calibration element 19 and again conducts the pressure level sensing procedure in order to determine the height (Z) at this new position over the calibration element 19. Each pre-determined step for the dispenser 340 in the Y-direction and its respective level sense height measurement (Z) is shown in phantom lines in FIG. 14B.

Once the dispenser 340 has moved through all of its predetermined Y-direction steps, the control system 410 identifies the two-dimensional coordinate resulting in the greatest distance or height ($Z_{max}$) between the dispenser 340 (distal portion of metering tip 102) to the lowest point on the surface of the calibration element 19. This coordinate is identified by the control system as ($Y_{opt}, Z_{max}$) and this coordinate value is stored in the memory of the control system 410.

At this point, for those portions or components of the analyzer 10 that have movement in a third-dimension such as the X-direction, the analyzer portion or component is moved or stepped a pre-determined distance in the X-direction while the dispenser 340 is held in position in the Y-dimension or direction (the Y coordinate value $Y_{opt}$ is held constant). Again, the pressure level sensing procedure in accordance with the present invention is conducted for each predetermined step in the X-direction wherein the distance or height (Z) between the dispenser 340 and the surface of the calibration element 19 is detected and measured by level sensing. The control system 410 identifies and stores all coordinate values (Xi, $Y_{opt}, Z_i$) and further identifies a three-dimensional coordinate wherein the Z-coordinate (height) is at its maximum ($Z_{max}$) This coordinate is identified by the control system 410 as ($X_{opt}, Y_{opt}, Z_{max}$) and is referred to as an alignment point A, for this particular component or portion of the analyzer 10.

Accordingly, the calibration method in accordance with the present invention is repeated for all desired portions or stations such as P1–P13 (FIG. 1) utilizing the appropriate calibration element 19 for each of these stations that interface and interact with the dispenser 340 and metering tip 102 during regular operation of the analyzer 10. After all calibration steps have been completed in accordance with the algorithm (FIG. 15) and method outlined above, the control system 410 of the analyzer 10 automatically aligns the dispenser 340 and metering tip 102 at all desired and pre-determined locations or stations (P1–P13) of the analyzer 10 during normal operation.

By way of example, the calibration and automatic alignment method in accordance with the present invention is utilizable for aligning the dispenser 340 and metering tip 102 in automatic alignment with the optimum dispensing location ($X_{opt}, Y_{opt}, Z_{max}$) for the sample tray 16 as best shown in FIG. 13. In this example, the automatic alignment of the dispenser 340 and metering tip 102 at the sample container 18 is calibrated by utilizing a calibration element 19 (FIGS. 14B and 14B) in the form of the sample container 18. Thus, the calibration element 19 is placed in the sample tray 16 at a location within the sample tray 16 along the metering line L as shown in FIG. 13.

The control system 410 then steps the dispenser 340 of the metering system 30 along the metering line L such that the dispenser 340 and metering tip 102 are positioned at a location over the calibration element 19. As outlined above, movement across the metering line L is in Y coordinate direction as shown. Once the dispenser 340 is positioned near the calibration element 19, the pressure level sensing technique is utilized in the manner described above. Pressure measurements are made and translated to a height value (Z) until the lowest point or greatest height ($Z_{max}$) is identified and stored in the software (memory) of the control system 410. At this point, the position coordinate is stored as ($Y_{opt}$, $Z_{max}$) While the dispenser 340 is held at the Y position, the sample tray 16 is rotated in direction R resulting in a movement of the sample container location (occupied by the calibration element 19) in the X coordinate direction. And, in accordance with the steps outlined above, additional height measurements are made by the level sensing technique until the greatest height distance is determined ($Z_{max}$). As mentioned above, this coordinate location is identified and stored in the memory (software) of the control system 410 as three-dimensional coordinate ($X_{opt}$, $Y_{opt}$, $Z_{max}$) for the sample container 18 and is identified as the alignment point A for this portion of the clinical analyzer 10 when the clinical analyzer 10 is operating under normal conditions.

Accordingly, in operation, the clinical analyzer 10 brings dispenser 340 to alignment point A (position coordinate $X_{opt}$, $Y_{opt}$, $Z_{max}$) to the sample container 18 of the sample tray 16 every time sample is required to be aspirated with the dispenser 340. Likewise, since the calibration method in accordance with the present invention is conducted for all desired stations, for example stations P1–P13, the clinical analyzer 10 moves the dispenser 340 to the alignment point A for each of these stations or components during regular operation prior to activating, e.g. aspirating or dispensing, the dispenser 340.

It will be apparent that other modifications and variations are possible which employ the inventive concepts of the present invention. For example, the above described auxiliary sample handler can be used in connection with a combinational analyzer having multiple chemistry stations or the handler can include additional aspiration stations, for example, to permit dilution of an assay of a dry chemistry system.

What is claimed is:

1. A method for calibrating a clinical analyzer having a dispenser, the method comprising the steps of:
   (a) loading a calibration element at a portion of the clinical analyzer;
   (b) moving a dispenser of the clinical analyzer in a pre-determined direction (Y) to a position over the calibration element;
   (c) measuring the height (Z) from the dispenser to the calibration element and determining a position coordinate ($Y_i$, $Z_i$);
   (d) storing the position coordinate ($Y_i$, $Z_i$) and repeating steps (b)–(d);
   (e) determining a maximum height ($Z_{max}$) for the dispenser positioned over the calibration element defined as position coordinate ($Y_{opt}$, $Z_{max}$); and
   (f) storing the position coordinate including the maximum height ($Z_{max}$) for the dispenser positioned over the calibration element.

2. The method according to claim 1, including repeating steps (b)–(d) for a plurality of pre-determined steps in the Y direction.

3. The method according to claim 2, including moving the portion of the clinical analyzer in the X-direction and measuring the height (Z) from the dispenser to the calibration element and determining a position coordinate ($X_i$, $Y_{opt}$, $Z_i$).

4. The method according to claim 3, including determining the maximum height ($Z_{max}$) for the dispenser positioned over the calibration element defined as position coordinate ($X_{opt}$, $Y_{opt}$, $Z_{max}$).

5. The method according to claim 4, including storing the position coordinate ($X_{opt}$, $Y_{opt}$, $Z_{max}$) as an alignment point for the dispenser.

6. The method according to claim 5, including operating the clinical analyzer by activating the dispenser at the alignment point.

7. The method according to claim 5, including repeating step (a) for another portion of the clinical analyzer and repeating all steps for the other portion of the clinical analyzer.

8. The method according to claim 7, including operating the clinical analyzer by activating the dispenser at the alignment point.

9. The method according to claim 2, including measuring the height (Z) of the dispenser to the calibration element by pressure level sensing with the dispenser.

10. The method according to claim 2, including loading the calibration element at a sample tray in step (a) and defining the portion of the clinical analyzer as the sample tray.

11. The method according to claim 2, including loading the calibration element at a portion of the clinical analyzer in step (a) defined as a primary metering point.

12. The method according to claim 2, including loading the calibration element at a portion of the clinical analyzer in step (a) defined as a reflex metering point.

13. The method according to claim 2, including loading the calibration element at a portion of the clinical analyzer in step (a) defined as a STAT metering point.

14. The method according to claim 2, including loading the calibration element at a portion of the clinical analyzer in step (a) defined as a thin film metering point.

15. The method according to claim 2, including loading the calibration element at a portion of the clinical analyzer in step (a) defined as a tip seal.

16. The method according to claim 2, including loading the calibration element at a portion of the clinical analyzer in step (a) defined as a first tip pick-up point.

17. The method according to claim 2, including loading the calibration element at a portion of the clinical analyzer in step (a) defined as a first tip eject point.

18. The method according to claim 2, including loading the calibration element at a portion of the clinical analyzer in step (a) defined as a second cuvette metering point.

19. The method according to claim 2, including loading the calibration element at a portion of the clinical analyzer in step (a) defined as a second tip pick-up point.

20. The method according to claim 2, including loading the calibration element at a portion of the clinical analyzer in step (a) defined as a cuvette metering point.

21. The method according to claim 2, including loading the calibration element at a portion of the clinical analyzer in step (a) defined as a micro-tip pick-up point.

22. The method according to claim 2, including loading the calibration element at a portion of the clinical analyzer in step (a) defined as a second tip eject point.

23. The method according to claim 2, including loading the calibration element at a portion of the clinical analyzer in step (a) defined as a wet reagent metering point.

24. The method according to claim 2, wherein step (a) includes a calibration element in the form of a test tube.

25. The method according to claim 2, wherein step (a) includes a calibration element in the form of a sample container.

26. The method according to claim 2, wherein step (a) includes a calibration element in the form of a reagent container.

27. The method according to claim 2, wherein step (a) includes a calibration element in the form of an Eppendorf tube.

28. The method according to claim 1, including using a control system for steps (b)–(f).

29. A method for automatically aligning a dispenser of a clinical analyzer, the method comprising the steps of:
(a) loading a calibration element at a portion of the clinical analyzer;
(b) moving a dispenser of the clinical analyzer in a pre-determined direction (Y) to a position over the calibration element;
(c) measuring the height (Z) from the dispenser to the calibration element and determining a position coordinate ($Y_i, Z_i$);
(d) storing the position coordinate ($Y_i, Z_i$) and repeating steps (b)–(d);
(e) determining a maximum height ($Z_{max}$) for the dispenser positioned over the calibration element defined as position coordinate ($Y_{opt}, Z_{max}$); and
(f) storing the position coordinate including the maximum height ($Z_{max}$) for the dispenser positioned over the calibration element.

30. The method according to claim 29, including repeating steps (b)–(d) for a plurality of pre-determined steps in the Y direction.

31. The method according to claim 30, including moving the portion of the clinical analyzer in the X-direction and measuring the height (Z) from the dispenser to the calibration element and determining a position coordinate ($X_i, Y_{opt}, Z_i$).

32. The method according to claim 31, including determining the maximum height ($Z_{max}$) for the dispenser positioned over the calibration element defined as position coordinate ($X_{opt}, Y_{opt}, Z_{max}$).

33. The method according to claim 32, including storing the position coordinate ($X_{opt}, Y_{opt}, Z_{max}$) as an alignment point for the dispenser.

34. The method according to claim 33, including operating the clinical analyzer by activating the dispenser at the alignment point.

35. The method according to claim 33, including repeating step (a) for another portion of the clinical analyzer and repeating all steps for the other portion of the clinical analyzer.

36. The method according to claim 35, including operating the clinical analyzer by activating the dispenser at the alignment point.

37. The method according to claim 30, including measuring the height (Z) of the dispenser to the calibration element by pressure level sensing.

38. The method according to claim 30, including loading the calibration element at a sample tray in step (a) and defining the portion of the clinical analyzer as the sample tray.

39. The method according to claim 30, including loading the calibration at a portion of the clinical analyzer in step (a) defined as a primary metering point.

40. The method according to claim 30, including loading the calibration at a portion of the clinical analyzer in step (a) defined as a reflex metering point.

41. The method according to claim 30, including loading the calibration at a portion of the clinical analyzer in step (a) defined as a STAT metering point.

42. The method according to claim 30, including loading the calibration at a portion of the clinical analyzer in step (a) defined as a thin film metering point.

43. The method according to claim 30, including loading the calibration at a portion of the clinical analyzer in step (a) defined as a tip seal.

44. The method according to claim 30, including loading the calibration at a portion of the clinical analyzer in step (a) defined as a first tip pick-up point.

45. The method according to claim 30, including loading the calibration at a portion of the clinical analyzer in step (a) defined as a first tip eject point.

46. The method according to claim 30, including loading the calibration at a portion of the clinical analyzer in step (a) defined as a second cuvette metering point.

47. The method according to claim 30, including loading the calibration at a portion of the clinical analyzer in step (a) defined as a second tip pick-up point.

48. The method according to claim 30, including loading the calibration at a portion of the clinical analyzer in step (a) defined as a cuvette metering point.

49. The method according to claim 30, including loading the calibration at a portion of the clinical analyzer in step (a) defined as a micro-tip pick-up point.

50. The method according to claim 30, including loading the calibration at a portion of the clinical analyzer in step (a) defined as a second tip eject point.

51. The method according to claim 30, including loading the calibration at a portion of the clinical analyzer in step (a) defined as a wet reagent metering point.

52. The method according to claim 30, wherein step (a) includes a calibration element in the form of a test tube.

53. The method according to claim 30, wherein step (a) includes a calibration element in the form of a sample container.

54. The method according to claim 30, including loading the calibration at a portion of the clinical analyzer in step (a) defined as a reagent container.

55. The method according to claim 30, including loading the calibration at a portion of the clinical analyzer in step (a) defined as an Eppendorf tube.

56. The method according to claim 29, including using a control system for steps (b)–(f).

* * * * *